(12) United States Patent
Klenner (10) Patent No.: US 12,272,913 B2
(45) Date of Patent: Apr. 8, 2025

(54) CLIP FOR MAKING A MECHANICAL AND ELECTRICALLY CONDUCTIVE CONNECTION BETWEEN THE CLIP AND A PIN, ESPECIALLY A FEEDTHROUGH PIN

(71) Applicant: BIOTRONIK SE & Co. KG, Berlin (DE)

(72) Inventor: Rolf Klenner, Michendorf (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/709,985

(22) Filed: Mar. 31, 2022

(65) Prior Publication Data
US 2022/0224026 A1 Jul. 14, 2022

Related U.S. Application Data

(63) Continuation of application No. 16/190,220, filed on Nov. 14, 2018, now abandoned.

(30) Foreign Application Priority Data

Nov. 21, 2017 (DE) ...................... 10 2017 127 391.3
Jul. 6, 2018 (DE) ...................... 10 2018 211 199.5

(51) Int. Cl.
*H05K 5/02* (2006.01)
*A61N 1/375* (2006.01)
(Continued)

(52) U.S. Cl.
CPC ............. *H01R 4/48* (2013.01); *A61N 1/3754* (2013.01); *A61N 1/378* (2013.01); *H01R 4/029* (2013.01);
(Continued)

(58) Field of Classification Search
CPC ........ H01R 4/48; H01R 4/029; H01R 4/4809; H01R 13/112; H01R 2201/12;
(Continued)

(56) References Cited

U.S. PATENT DOCUMENTS 4,547,036 A * 10/1985 Keglewitsch .......... H01H 85/24
439/842
5,144,946 A * 9/1992 Weinberg ............. A61N 1/3758
607/2
(Continued)

FOREIGN PATENT DOCUMENTS

CN 103547058 A 1/2014
JP 06031472 A * 2/1994
(Continued)

OTHER PUBLICATIONS

Translation of JP-06031472-A (Year: 1994).*
Translation of JP-2009206025-A (Year: 2009).*

*Primary Examiner* — Abhishek M Rathod
(74) *Attorney, Agent, or Firm* — Buchanan Ingersoll & Rooney PC (57) ABSTRACT

A clip for making a mechanical and electrically conductive connection between the clip and an electrically conductive pin. The clip has a base, and a first arm and an opposite second arm projecting out from the base. The first and the second arms each having a clipping area, the clipping areas of the first and second arms running toward one another and being designed to lie against the pin to make the mechanical and electrically conductive connection when the pin is arranged between the clipping areas of the first and second arms, respectively. A centering area departs from each of the clipping areas, that is, the clipping area of the first arm and the clipping area of the second arm, the centering area of the first arm and the centering area of the second arm diverging from one another.

10 Claims, 6 Drawing Sheets

(51) Int. Cl.
*A61N 1/378* (2006.01)
*H01R 4/02* (2006.01)
*H01R 4/48* (2006.01)
*H01R 13/11* (2006.01)
*A61N 1/36* (2006.01)
*A61N 1/362* (2006.01)
*A61N 1/39* (2006.01)

(52) U.S. Cl.
CPC ......... *H01R 4/4823* (2023.08); *H01R 4/4848* (2023.08); *H01R 13/112* (2013.01); *H05K 5/0247* (2013.01); *A61N 1/3605* (2013.01); *A61N 1/362* (2013.01); *A61N 1/3956* (2013.01); *H01R 2201/12* (2013.01)

(58) Field of Classification Search
CPC .... A61N 1/3754; A61N 1/378; A61N 1/3605; A61N 1/362; A61N 1/3956; H05K 5/0247
See application file for complete search history.

(56) References Cited

U.S. PATENT DOCUMENTS

| | | | | |
|---|---|---|---|---|
| 5,391,098 | A | * | 2/1995 | Ohashi ................ H01H 85/202 439/78 |
| 5,451,921 | A | * | 9/1995 | Crawford ............ H01C 1/1406 338/332 |
| 6,662,035 | B2 | | 12/2003 | Sochor |
| 6,837,755 | B1 | * | 1/2005 | Kitajima ............. H01R 43/205 439/830 |
| 7,085,139 | B2 | * | 8/2006 | Chen .................... H01Q 1/1207 439/830 |
| 7,647,110 | B2 | * | 1/2010 | Hornfeldt ............. A61N 1/375 607/116 |
| 7,736,191 | B1 | * | 6/2010 | Sochor ................. H01R 24/58 607/116 |
| 8,412,330 | B2 | * | 4/2013 | Kast .................... A61N 1/3752 607/37 |
| 9,126,053 | B2 | * | 9/2015 | Kempf ................ A61N 1/3754 |
| 9,227,052 | B2 | | 1/2016 | Robnett |
| 9,882,293 | B1 | * | 1/2018 | Chen .................... H01R 9/053 |
| 9,931,513 | B2 | | 4/2018 | Kelsch et al. |
| 2003/0069612 | A1 | * | 4/2003 | Zart .................... B29C 45/1618 607/36 |
| 2006/0094297 | A1 | | 5/2006 | Wang |
| 2009/0017700 | A1 | | 1/2009 | Zart et al. |
| 2009/0192578 | A1 | * | 7/2009 | Biggs .................. A61N 1/3752 607/116 |
| 2010/0203776 | A1 | * | 8/2010 | Zhao .................... H01R 4/48 439/840 |
| 2010/0240253 | A1 | * | 9/2010 | Kast .................... A61N 1/0551 29/857 |
| 2012/0142211 | A1 | * | 6/2012 | Kubo .................... H01R 24/40 439/585 |
| 2013/0338750 | A1 | * | 12/2013 | Eck ...................... A61N 1/3754 439/271 |
| 2015/0325929 | A1 | * | 11/2015 | Okura .................. H01R 4/26 439/444 |
| 2016/0129264 | A1 | * | 5/2016 | Hovland ............... H01M 50/55 607/116 |
| 2016/0134029 | A1 | * | 5/2016 | Kim .................... H01R 4/28 439/816 |
| 2016/0150685 | A1 | * | 5/2016 | Kurita .................. H05K 9/0016 174/384 |
| 2016/0220827 | A1 | * | 8/2016 | Bunyan ................ A61N 1/3754 |
| 2016/0315302 | A1 | * | 10/2016 | Aamodt ................ A61N 1/3756 |
| 2017/0245386 | A1 | * | 8/2017 | Park .................... H04M 1/0277 |
| 2017/0325741 | A1 | * | 11/2017 | Lim ...................... A61B 5/29 |
| 2018/0042552 | A1 | * | 2/2018 | Li ........................ A61B 5/076 |
| 2018/0140853 | A1 | * | 5/2018 | Maile .................. A61N 1/37229 |
| 2018/0145427 | A1 | * | 5/2018 | Otsu .................... H01R 4/48 |

FOREIGN PATENT DOCUMENTS

| | | | |
|---|---|---|---|
| JP | H0631472 | A | 2/1994 |
| JP | H0690093 | A | 3/1994 |
| JP | 2005114759 | A | 4/2005 |
| JP | 2009206025 | A * | 9/2009 |
| KR | 101324610 | B1 | 11/2013 |
| KR | 101386071 | B1 | 4/2014 |

\* cited by examiner

CLIP FOR MAKING A MECHANICAL AND ELECTRICALLY CONDUCTIVE CONNECTION BETWEEN THE CLIP AND A PIN, ESPECIALLY A FEEDTHROUGH PIN

CROSS-REFERENCE TO RELATED APPLICATIONS

This application is a continuation application of co-pending U.S. application Ser. No. 16/190,220, filed on Nov. 14, 2018, which claims the priority, under 35 U.S.C. § 119, of German applications DE 10 2017 127 391.3, filed Nov. 21, 2017, and DE 10 2018 211 199.5, filed Jul. 6, 2018; all of which are hereby incorporated by reference in their entireties.

BACKGROUND OF THE INVENTION

Field of the Invention

The invention relates to a clip for making a mechanical and electrically conductive connection between the clip and an electrically conductive pin, which may, for instance, be an electrical feedthrough of a medical device.

The known systems that have been proposed up to now as solutions for the connection of external wiring do not, as a rule, use clip contacts. This often has to do with the fact that clip contacts present the technical challenge of pushing the complete subassembly with which contact is to be made in the perpendicular direction onto the feedthrough pin to achieve an axial clip contact.

By contrast, U.S. Pat. No. 7,736,191 B1 describes clip contacts for connecting a neuroelectrode at the proximal end, the respective clip contact having a contact protection element and a contact element that is passed through the contact protection element on both sides, which represents a comparatively complex design.

SUMMARY OF THE INVENTION

Therefore, starting from the prior art presented above, this invention has the goal of making available a clip for making a mechanical and electrically conductive connection with a pin, this clip having a comparatively simple structure and allowing, in particular, the locking of external wiring bands in medical devices (e.g., pacemakers, implantable cardioverter-defibrillators (ICD), neurostimulators) that have a feedthrough with round pins, or this clip being reliably usable in the available space of a medical device (especially of an implant).

With the above and other objects in view there is provided, in accordance with the invention clip for making a mechanical and electrically conductive connection between the clip and an electrically conductive pin. The novel clip comprises:

a base;

a first arm and a second arm opposite the first arm, the first and the second arms projecting out from the base, and each of the first and second arms having a clipping area;

the clipping area of the first arm and the clipping area of the second arm running toward one another and being configured to lie against the pin to make the mechanical and electrically conductive connection when the pin is disposed between the clipping area of the first arm and the clipping area of the second arm; and a centering area respectively departing from each of the clipping area of the first arm and the clipping area of the second arm, the centering area of the first arm and the centering area of the second arm diverging from one another.

In other words, the invention provides for a clip that is configured for making a mechanical and electrically conductive connection between the clip and an electrically conductive pin (especially an electrical feedthrough of a medical device), and that has at least:

a base or base area, and a first arm and an opposite second arm, the first and the second arms each sticking out from the base, the first and the second arms each having a clipping area, the clipping area of the first arm and the clipping area of the second arm running toward one another and being designed to lie against the pin to make the mechanical and electrically conductive connection, if the pin is arranged between the clipping area of the first arm and the clipping area of the second arm, and a centering area departing from each of the clipping areas, that is, the clipping area of the first arm and the clipping area of the second arm, the centering area of the first arm and the centering area of the second arm diverging from one another starting at the respective clipping area.

In particular, the invention allows the locking of external wiring bands in known products (for example, pacemakers, ICDs, neurostimulators) that have a feedthrough with round or cylindrical pins. This keeps the bands in a secure position until the welding process. This also allows blind welding, since the relative position between band and pin is unambiguous. Thus, the final subassembly achieves a non-detachable connection while simplifying assembly.

In contrast to a classic plug contact, the inventive clip can be put on in the direction transverse to the pin. The second main purpose is especially to make the clip SMT solderable (e.g., by gold plating a surface or connection area of the clip) and to place it on a circuit or substrate as an SMT component. This makes it possible, e.g., to connect a battery directly to a circuit, without an additional wiring band.

Especially since the inventive clip can surround the pin in the direction transverse to the axial direction of the pin, this produces self-locking, which allows clearly simplified handling of the subsequent processes. In the same way, it is possible to omit the welding altogether in the area of the external wiring. This does not increase the existing size, as is the case in axial plug-and-socket connections.

Furthermore, the internal design can advantageously do without complete battery wiring, [since] the pins of the battery can be inserted directly into the clips. This solution provides perpendicular assembly (for simple automation).

One embodiment of the inventive clip provides that the clipping area of the first arm and the centering area of the first arm be made together as an integral part. It is also preferably provided that the clipping area of the second arm and the centering area of the second arm also be made together as an integral part.

One embodiment of the inventive clip provides that the clipping area of the first arm and the clipping area of the second arm be designed to press the pin against the base if the pin is arranged between the two clipping areas as it is supposed to be.

One embodiment of the inventive clip further provides that the clipping area of the first arm and the clipping area of the second arm be designed to be pretensioned against the pin to make the said connection or to clip the pin, if the pin is arranged between the clipping area of the first arm and the clipping area of the second arm, as it is supposed to be. In particular, this involves the pin also being pressed against the base, as described above, so that it makes contact with it.

One embodiment of the inventive clip further provides that the centering area of the first arm and the centering area of the second arm each have an inner surface, the inner surface of the centering area of the first arm facing the inner surface of the centering area of the second arm, and the first arm and the second arm being configured so that pressing the pin against the facing inner surfaces of the centering areas of the first and the second arms presses the first arm and the second arm apart, so that the pin can be placed between the clipping area of the first arm and the clipping area of the second arm.

One preferred embodiment of the inventive clip further provides that the first arm and the second arm or the corresponding clipping areas be made as an integral part with the base. In particular, this involves providing that the first arm and the second arm be made together as an integral part through the base, i.e., that they are formed from one piece together with the base.

One embodiment of the inventive clip further provides that the clip be formed from a flat sheet metal element by shaping this sheet metal element. This makes it simple to produce the above-described integral design of the clip and centering areas of the arms and to produce the integral design of the arms (or clipping areas) with the base.

One embodiment of the inventive clip further provides that the clip have another base that is connected, through a connection area, with the other base described at the beginning.

One embodiment preferably provides that the two bases be made together as an integral part through the connection area.

One embodiment of the inventive clip further provides that the clip have a third arm and an opposite fourth arm. Here it is preferably provided that the third and the fourth arms each have a clipping area, the clipping area of the third arm and the clipping area of the fourth arm running toward one another and being designed to lie against the pin to make the mechanical and electrically conductive connection, if the pin is arranged between the clipping area of the third arm and the clipping area of the fourth arm. One embodiment further provides that a centering area depart from each of the clipping areas, that is the clipping area of the third arm and the clipping area of the fourth arm, the centering area of the third arm and the centering area of the fourth arm once again diverging from one another starting at the respective clipping area.

One embodiment of the invention further provides that the third and the fourth arms each stick out from the other base.

One embodiment of the inventive clip further provides that the clipping area of the third arm and the centering area of the third arm be made together as an integral part. It is also preferably provided that the clipping area of the fourth arm and the centering area of the fourth arm also be made together as an integral part.

The integral design of the two bases (through the connection area) and the integral design of the clip and centering areas of the third or fourth arms and the integral design of the third and fourth arms (or the corresponding clipping areas) with the other base are also simple to realize by forming the clip by shaping a correspondingly flat sheet metal element.

One embodiment of the inventive clip further provides that the clipping area of the third arm and the clipping area of the fourth arm also be designed to be pretensioned against the pin to make the said connection or to clip the pin, if the pin is arranged between the clipping area of the third arm and the clipping area of the fourth arm, as they are supposed to be.

One embodiment of the inventive clip further provides that the centering area of the third arm and the centering area of the fourth arm each have an inner surface, the inner surface of the centering area of the third arm facing the inner surface of the centering area of the fourth arm, and the third arm and the fourth arm being configured so that pressing the pin against the facing inner surfaces of the centering areas of the third arm and the fourth arm presses the third arm and the fourth arm apart, so that the pin can be placed between the clipping area of the third arm and the clipping area of the fourth arm.

One embodiment of the inventive clip further provides that the base through which the first arm is connected with the second arm form a welding area through which the clip can be welded with the pin if the pin is arranged between the clipping area of the first arm and the clipping area of the second arm. One embodiment further provides that the other base through which the third arm is connected with the fourth arm also form another welding area through which the clip can be welded with the pin if the pin is arranged between the clipping area of the third arm and the clipping area of the fourth arm.

One embodiment of the inventive clip further provides that the base have a front surface that faces the pin if the pin is arranged between the clipping area of the first arm and the clipping area of the second arm, and a back surface that faces away from the front surface of the base, the back surface of the base being in the form of a solderable connection surface. One embodiment further provides that the other base also have a front surface that faces the pin if the pin is arranged between the clipping area of the third arm and the clipping area of the fourth arm, and a back surface that faces away from the front surface of the other base, the back surface of the other base also being in the form of a solderable connection surface.

That is, the connection surface or back surface of the base or of the other base of the clip are each designed in particular to be soldered with a corresponding contact surface of a substrate, especially a circuit board. To accomplish this, the said back surface of the base or of the other base can, in particular, be coated so that it is SMT solderable.

For the case in which the clip has four arms and accordingly a connection area that connects the two bases with one another together, one embodiment of the inventive clip provides that the connection area have a front surface that faces the pin if the pin is arranged between the clipping areas of the arms, the front surface of the connection area being convexly curved to make contact with the pin. In the case of such a clip with four arms, one embodiment can provide that if the pin is arranged between the clipping areas in the way it is supposed to be, it only makes contact with the clipping areas and the connection area, however not with the bases. The back surface of the connection area facing away from the front surface of the connection area can be concavely curved.

Furthermore, the connection area can be in the form of a spring element that is configured to be pretensioned against the pin if the pin is arranged between the clipping areas of the arms of the clip, in particular this curvature decreasing if the front surface of the connection area or the spring area makes contact with the pin.

Another aspect of this invention relates to an arrangement with at least one inventive clip and at least one electrically conductive (especially cylindrical) pin, the at least one pin being clamped against the at least one clip by means of the clipping areas of the at least one clip, especially in one of the above-described ways.

One embodiment of the inventive arrangement provides that the at least one clip additionally be welded with the at least one pin (for example, through the welding area(s); see above).

Another embodiment of the inventive arrangement provides that the at least one pin be brought out of a component of a medical device (a so-called feedthrough pin).

One embodiment of the inventive arrangement further provides that the medical device be an implantable medical device.

One embodiment of the inventive arrangement further provides that the component be a housing of the medical device, in particular a housing to hold a battery and/or electrical components.

One embodiment of the inventive arrangement further provides that the clip make an electrically conductive and mechanical connection of the at least one pin with a header of the medical device, the medical device especially being a cardiac pacemaker, and the header especially being designed to be connected with at least one electrode of the cardiac pacemaker or the medical device.

An alternative embodiment of the inventive arrangement further provides that the clip be soldered with a contact of a substrate (e.g., circuit board) through the back surface of the base and/or through the back surface of the other base.

According to one embodiment of the inventive arrangement the substrate is preferably a substrate of a medical device, the substrate in particular being arranged in a housing of the medical device.

Furthermore, according to one embodiment of the arrangement the at least one pin can be a pin brought out of a battery, this pin having an electrically conductive connection, in particular being soldered, with the contact of the substrate, e.g., through the at least one clip (see above).

Another aspect of this invention relates to a medical device with at least one inventive clip, the medical device having at least one electrically conductive (especially cylindrical) pin, the at least one pin being clamped against the at least one clip by means of the clipping areas of the at least one clip.

One embodiment of the inventive medical device provides that the at least one clip additionally be welded with the at least one pin (for example, through the welding area(s); see above).

According to one embodiment of the inventive medical device, the medical device is an implantable medical device, especially an implantable cardiac pacemaker. However, the medical device can also be an implantable cardioverter-defibrillator (ICD), a neurostimulator, or another medical device.

According to one embodiment of the inventive (especially implantable) medical device, the at least one pin is brought out of a component of the medical device (that is, it is a so-called feedthrough pin).

According to one embodiment of the inventive medical device, the said component is a housing of the (especially implantable) medical device, especially a housing that holds a battery and/or electrical components of the medical device. The clip then makes, e.g., a mechanical and electrically conductive connection to a header of the medical device. In this case, the medical device can be, e.g., an implantable cardiac pacemaker, the header being designed for connection of an electrode of the cardiac pacemaker.

One embodiment of the medical device further provides that the medical device have at least one wiring band.

This at least one wiring band can be connected with the base and/or with the other base of the at least one clip; in particular the at least one wiring band can be designed to be an integral part with the base and/or with the other base of the at least one clip.

Furthermore, the at least one wiring band can have an electrically conductive connection with the header of the medical device or cardiac pacemaker.

According to an alternative embodiment of the medical device, the said component can be a battery of the (especially implantable) medical device.

According to one embodiment of the inventive medical device, the at least one clip can be soldered with a contact of a substrate (e.g., a circuit board) of the medical device through the back surface of the base and/or through the back surface of the other base.

Another aspect of the invention relates to a process for making a mechanical and electrically conductive connection between an inventive clip and at least one pin, the at least one pin being clamped against the clip by means of the clipping areas of the at least one clip.

One embodiment of the process provides that in order to clamp the at least one pin against the at least one clip (or to make the electrically conductive and mechanical connection between the at least one clip and the at least one pin), the at least one pin is arranged between the clipping area of the first arm and the clipping area of the second arm. Furthermore, to clamp the at least one pin against the at least one clip, the at least one pin is also arranged between the clipping area of the third arm and the clipping area of the fourth arm.

One embodiment of the process further provides that the at least one pin clamped against the clip be connected with the at least one clip through at least one welded connection.

One embodiment of the process further provides that there can be a welded connection between the at least one pin and the base or welding area of the at least one clip. One embodiment of the process further provides that there can be a welded connection between the at least one pin and the other base or other welding area of the at least one clip.

The individual embodiments of the inventive solution each relate to a clip or clip contact, in particular one that comes in contact with the respective pin in the transverse direction. That is, the clip can be brought close to the pin in the direction transverse to the axial direction of the pin and then surround the pin in the peripheral direction of the pin. This produces self-locking, which allows clearly simplified handling of the subsequent processes. In the same way, it is possible to omit the welding altogether in the area of the external wiring. This does not increase the existing size, as is the case in axial plug-and-socket connections.

This allows other advantages during assembly of the external wiring of implants. The bands can be fixed to the pins beforehand, however it is no longer necessary to hold the pins in position with a complex tool. This advantageously makes it possible for the medical devices/implants also to be assembled while they are standing upright, and no longer in the casting mold, as has been necessary up to now. This has clear space advantages. The internal design can do without complete battery wiring, since the pins of the battery can be inserted directly into the clips. This solution provides perpendicular assembly (for simple automation).

Other features which are considered as characteristic for the invention are set forth in the appended claims.

Although the invention is illustrated and described herein as embodied in a clip for making a mechanical and electrically conductive connection between the clip and a pin, especially a feedthrough pin, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 shows an embodiment of an inventive clip, focusing especially on external wiring. Here a clip with a bent shape is arranged, e.g., at the end of the pin of every wiring band, this clip having at least two arms, each of which consists of a capture area or centering area and a clipping area, and each of which sticks out from a base of the clip. The centering areas serve, in particular, to compensate for existing tolerances and to center the feedthrough pin (2 of FIG. 1) with respect to the clip (1 of FIG. 1). The clipping areas surround the pin and prevent, in particular, movement of the clip relative to the pin. The base provides, in particular, a durable electrical contact to the pin and can also, when required, be welded at this place to provide a material bonding connection. Tolerances in the axial direction of the pin are compensated;

FIG. 4 shows another embodiment of an inventive clip; in particular, the inventive clips here are not arranged on a band, but rather as individual components whose back surfaces are coated to make them solderable. In particular, here the clips are laid (possibly with a separate tab for automated placement) onto the respective substrate or onto the circuit, realizing a clip contact that functions transverse to the pin and that allows pins, e.g., pins of a battery, to be inserted into the clips. In particular, in this case the battery does not require any other auxiliary means such as connection pads or wiring bands.

DETAILED DESCRIPTION OF THE INVENTION

Figure 1:
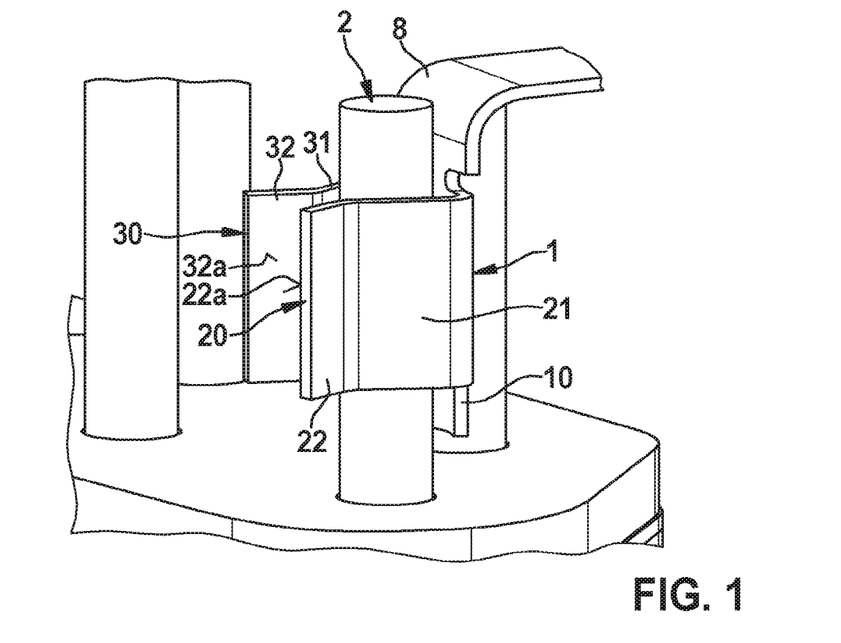

FIG. 1 shows a simple embodiment of an inventive clip 1 for making a mechanical and electrically conductive connection between the clip 1 and at least one electrically conductive pin 2. The clip 1 has a base 10, also referred to as a base area 10, and a first arm 20 and an opposite second arm 30, the first and the second arms 20, 30 each sticking out from the base area 10 and each having a clipping area 21, 31 and a centering area 22, 32 departing from each of the clipping areas 21, 31, the respective centering areas 22, 32 preferably being made as a single piece with or integrally connected with the associated clipping areas 21, 31. The base 10 can have a wiring band (also called a connection band) 8 connected to it, through which the clip 1 can have electrically conductive connection with an electrical contact or a component.

As is shown in FIG. 1, the clipping areas 21, 31 of the two arms 20, 30 run toward one another and are designed to lie against the pin 2 to make the mechanical and electrically conductive connection, if the pin 2 is arranged between the clipping area 21 of the first arm 20 and the clipping area 31 of the second arm 30, the clip 1 or the clipping areas 21, 31 together with the base 10 surrounding the pin 2 in the peripheral direction of the pin 2, that is, lying against it in the direction transverse to the pin 2, in particular the clipping areas 21, 31 being pretensioned against the pin 2. The pin 2 can additionally be connected through a welded connection with the base 10, which in this case forms a welding area.

The two centering areas 22, 32 diverge from one another starting at the respective clipping areas 21, 31. The centering area 22 of the first arm 20 and the centering area 32 of the second arm 30 each have an inner surface 22a, 32a, these inner surfaces 22a, 32a facing one another, the first arm 20 and the second arm 30 being configured, in particular, so that pressing the pin 2 in the direction transverse to the axial direction of the pin 2 against the facing inner surfaces 22a, 32a of the centering areas 22, 32 presses the first arm and the second arm apart, so that the pin 2 can be arranged between the clipping area 21 of the first arm 20 and the clipping area 31 of the second arm 30.

According to the FIGS. 2 through 5, an inventive clip can also have four arms 20, 30, 40, 50. In this case, it is, in particular, provided that the clip 1, as is shown, e.g., in FIGS. 2 and 3, have a further base 12, or base area 12, which is integrally connected into a single piece with the base area 10 through a connection area 11.

Figure 2:
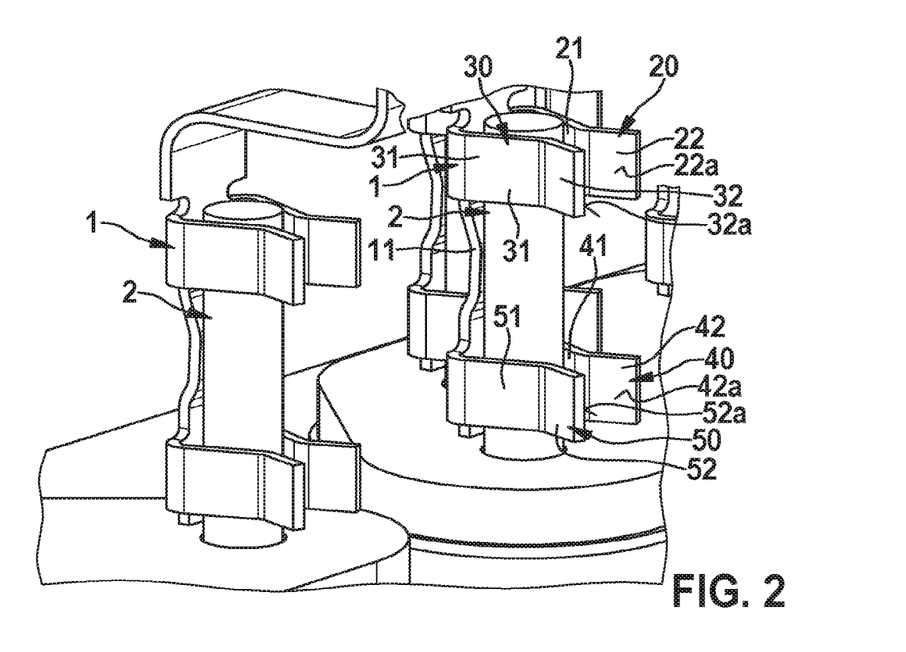
FIG. 2 shows another embodiment of clip according to the invention, focusing especially on external wiring. Here the inventive clip has four arms, each of which in turn has a centering area and a clipping area.
Figure 3:
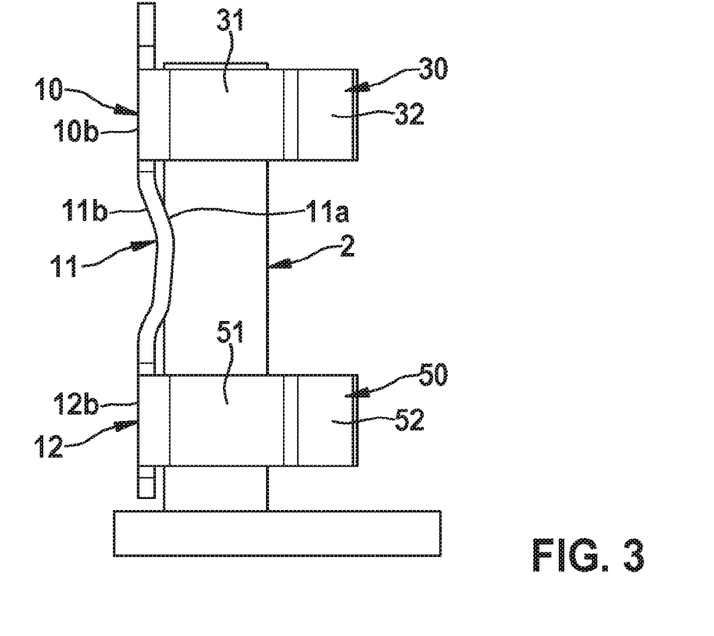
FIG. 3 shows another view of a clip of the type shown in FIG. 2.

As was already explained, the first and the second arms 20, 30 are connected with the base area 10, the additional third arm 40 and the additional fourth arm 50 departing from the further base area 12.

The third and the fourth arms 40, 50 each also have a clipping area 41, 51, the clipping area 41 of the third arm 40 and the clipping area 51 of the fourth arm 50 also running toward one another and being designed to lie against the pin 2 or to be pretensioned against it to make the mechanical and electrically conductive connection, if the pin 2 is arranged between the clipping area 41 of the third arm 40 and the clipping area 51 of the fourth arm 50. Furthermore, a centering area 42, 52 once again departs from each of the clipping areas, that is, the clipping area 41 of the third arm 40 and the clipping area 51 of the fourth arm 50, the centering area 42, 52 of the third arm 40 and the centering area 52 of the fourth arm 50 diverging starting from each of the associated clipping areas 41, 51.

The centering area 42 of the third arm 40 and the centering area 52 of the fourth arm 50 each also have an inner surface 42a, 52a, which serves to center or guide the pin 2 in the way described above for the two other arms 20, 30, if the pin 2 should be arranged between the clipping areas 41, 51.

Furthermore, the other base area 11 can also form a welding area, through which the clip 1 can additionally be weldable with the pin 2, if the pin 2 is arranged between the clipping area 41 of the third arm 40 and the clipping area 51 of the fourth arm 50, in the way it is supposed to be.

Especially in the case in which the clip 1 has four arms 20, 30, 40, 50, the connection area 11 can be in the form of a spring area or spring element, which makes an electrical contact with pin 2 and is pretensioned against it, if the pin 2 is arranged between the clipping areas 21, 31, 41, 51, as is shown in FIG. 3. To accomplish this, the connection area 11a can have front surface 11a, which faces the pin 2, if the pin 2 is arranged between the clipping areas 21, 31, 41, 51 of the arms 20, 30, 40, 50, the front surface 11a of the connection area 10 being convexly curved to make contact with the pin 2. The back surface 11b can be correspondingly concavely curved (cf. FIG. 3).

Figure 6:
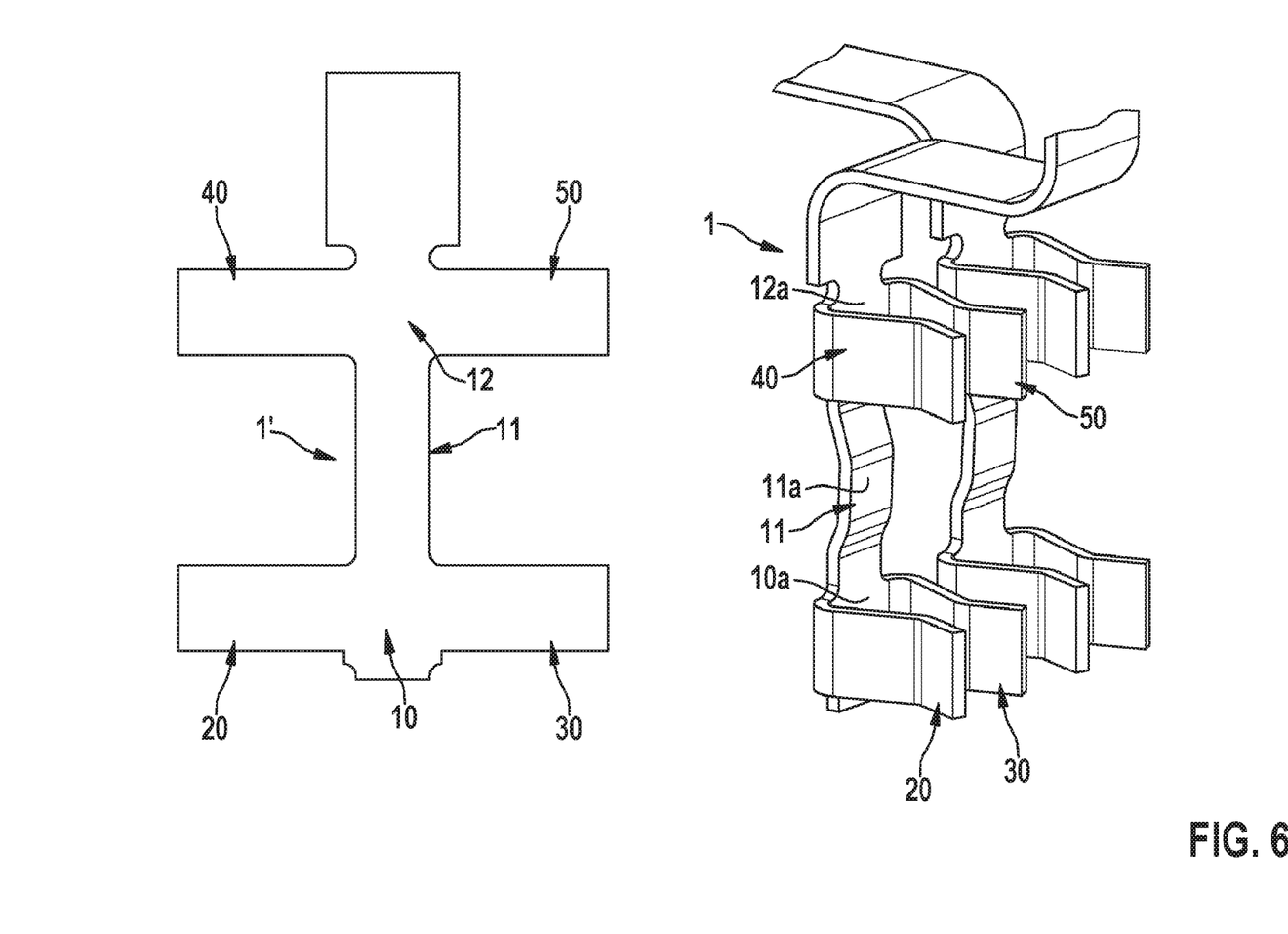
FIG. 6 shows, on the left, a flat sheet metal element from which an inventive clip of the type shown in FIG. 2 or 5 can be produced by shaping the sheet metal element; on the right side, two shaped sheet metal elements or clips are shown.

Each of the inventive clips 1 can be bent in the way shown in FIG. 6 from a sheet metal element 1' that has the respective arms 20, 30, 40, 50 as projections. In the case of the clip 1 according to FIG. 1, there are correspondingly only two projections for the arms 20, 30. This makes it extremely simple for the individual components 10, 11, 12, 20, 21, 22, 30, 31, 32, 40, 41, 42, 50, 51, 52 of the clip 1 to be realized as elements that are connected together or made as an integral part.

Figure 7A:
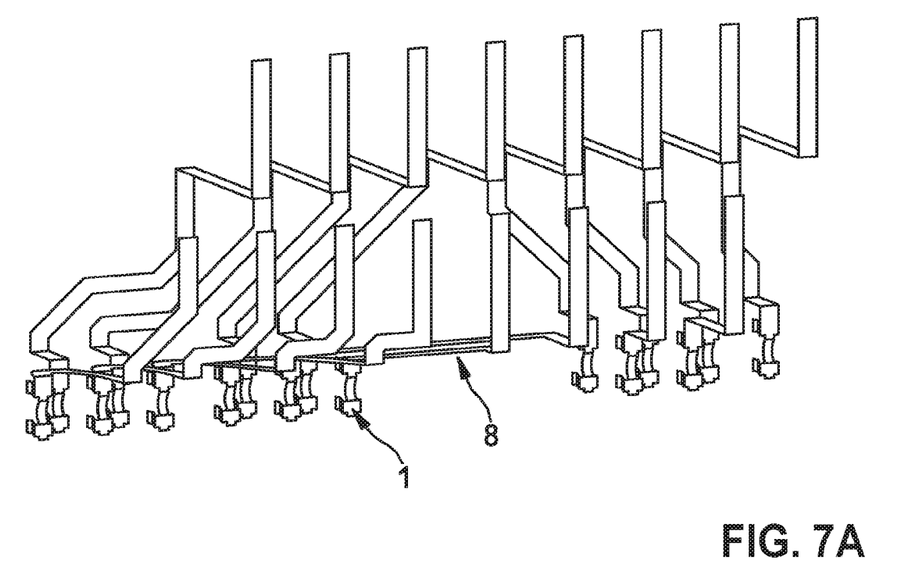
FIG. 7A shows a front view and FIG. 7B shows a rear view of a group of multiple clips with the electrical connection band.
Figure 7B:
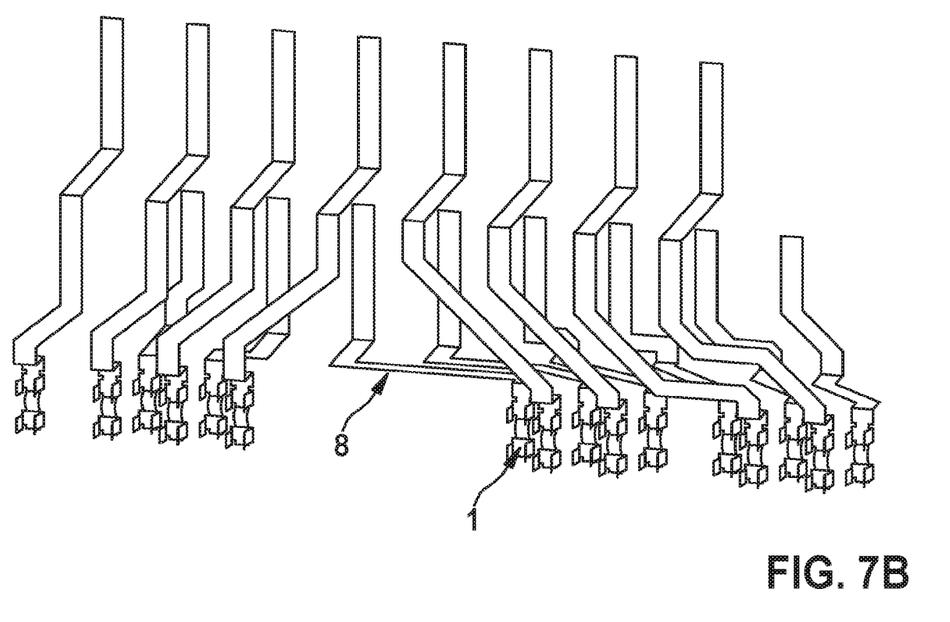

Multiple inventive clips 1 can advantageously be used as is shown in FIG. 7, to make a corresponding number of electrical and mechanical connections between individual pins 2 and wiring bands 8 associated with the clips 1.

Figure 8:
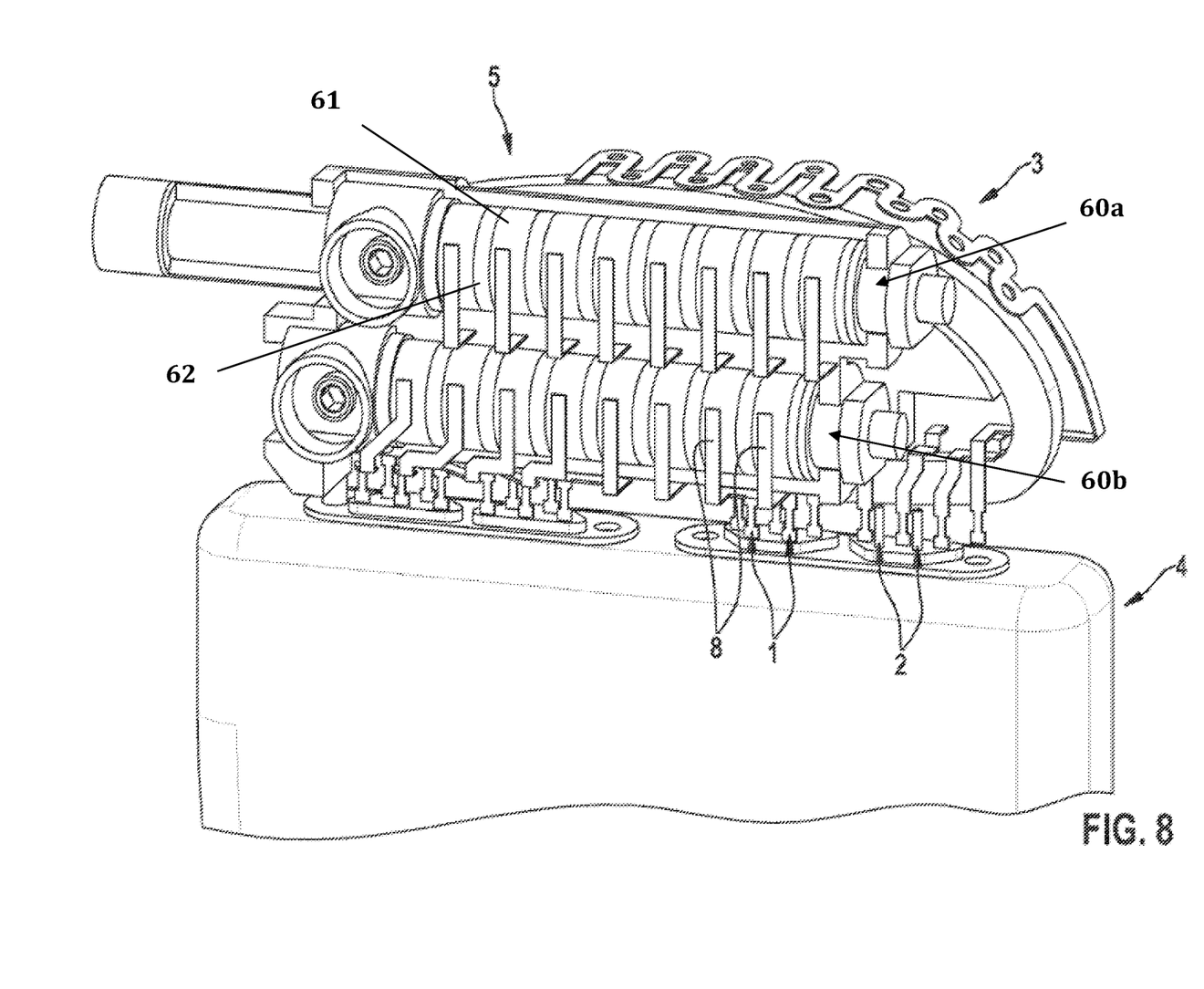
FIG. 8 shows an implantable medical device with inventive clips, the device shown here as an example being a neurostimulator.

This can be used especially in the case of implantable medical devices 3, such as, e.g., cardiac pacemakers 3, to make an electrical and mechanical connection, e.g., of the type shown in FIG. 8, between a header 5 of such a cardiac pacemaker 3 and the pins 2 that are brought out of a housing 4 (especially a battery housing 4). The individual wiring bands 8, each of which is preferably an integral part with a clip 1, have an electrically conductive connection with the header 5. FIG. 8 shows an implantable medical device 3 including two connection sockets 60a, 60b, each connection socket 60a, 60b having a plurality of annular electrical contacts 61 separated by sealing rings 62.

Figure 4:
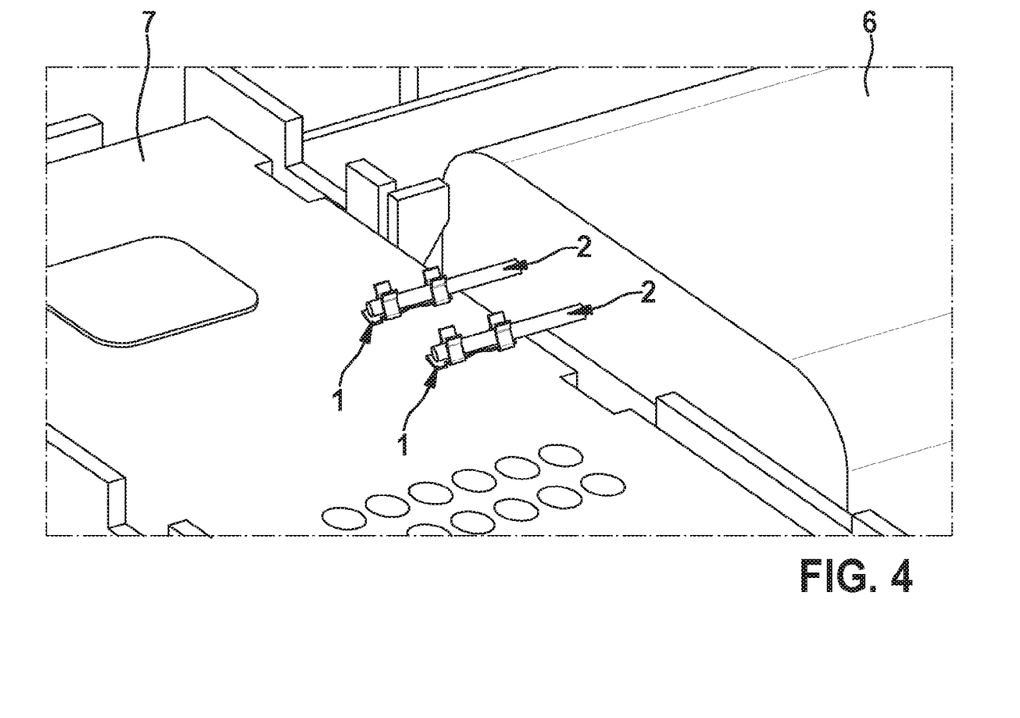
Figure 5:
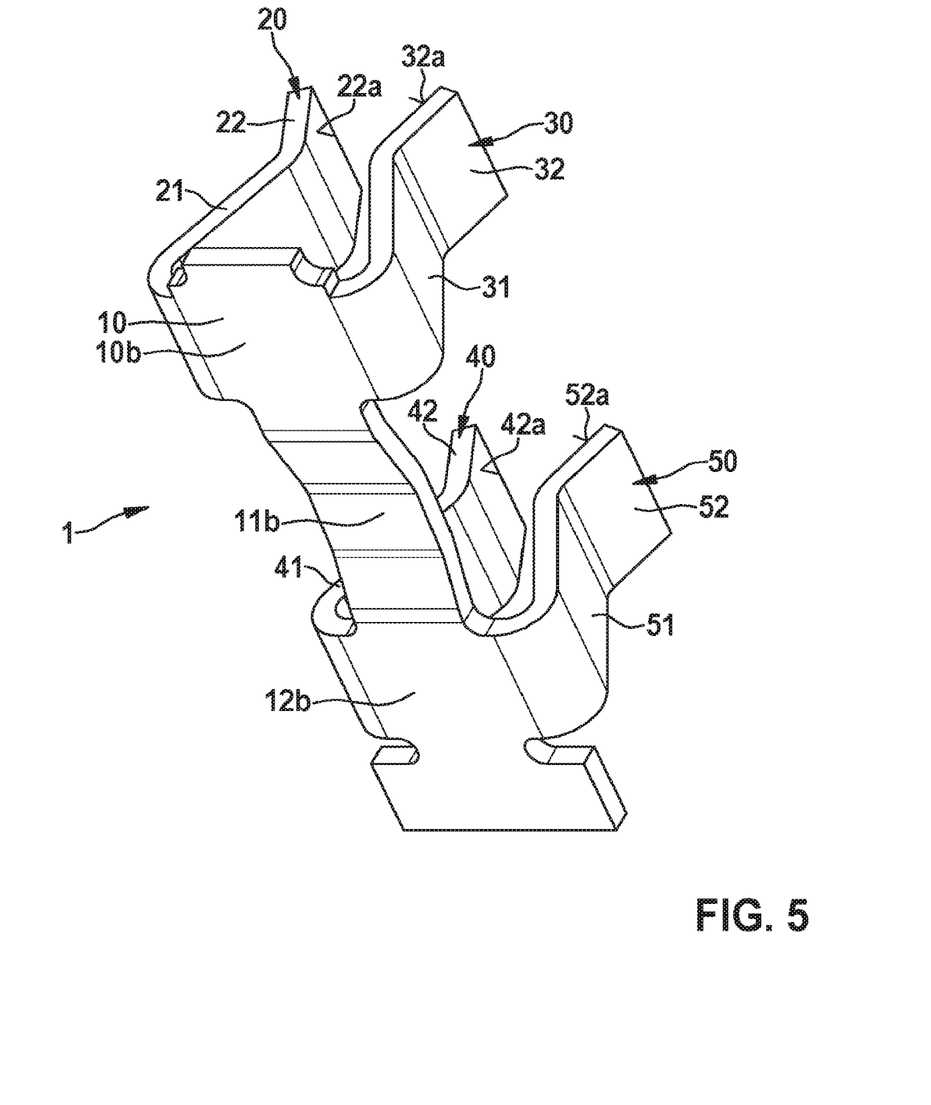
FIG. 5 shows a view of a clip of the type shown in FIG. 4, the back surfaces of the bases of the clip being coated to make them solderable, in particular SMT solderable, so that the respective clip can be used, e.g., in a standard population process for an electronic circuit.

FIGS. 4 and 5 show another application of the inventive clip concept. FIG. 5 provides that the respective base area 10, 12 have a back surface 10b, 12b (the front surfaces 10a, 12a are visible, e.g., in FIG. 6) that faces away from the pin 2 to be clipped, the back surfaces 10b, 12b being in the form of solderable connection surfaces, which therefore allow the respective clip 1 of the type shown in FIG. 4 to be arranged on a substrate 7 and to be soldered there with a corresponding electrical contact. In particular, this can be accomplished using an SMT process (SMT stands for Surface Mounted Technology). This makes it simple, e.g., to connect pins 2, which according to FIG. 4 are brought out of a battery 6, with the clip 1 associated with each of them. To accomplish this, the pins 2 only need to be inserted into the respective clip 1.

The invention claimed is:

1. A medical device comprising:
 a device housing having an electrical feedthrough comprising at least one electrically conductive pin, and
 a header portion comprising a connection socket configured to receive a plug of an electrode lead;
 the medical device further comprising:
 a clip configured to establish a mechanical and electrically conductive connection between the clip and the electrically conductive pin, the clip comprising:
 a base having a first side and a second side and a first end and a second end;
 a first arm and a second arm opposite said first arm, said first and the second arms projecting out from said first side and said second side, respectively, and each of said first and second arms having a clipping area;
 said clipping area of said first arm and said clipping area of said second arm running toward one another and being configured to lie against the pin to make the mechanical and electrically conductive connection when the pin is disposed between said clipping area of said first arm and said clipping area of said second arm;
 a centering area respectively departing from each of the clipping area of said first arm and said clipping area of said second arm, said centering area of said first arm and said centering area of said second arm diverging from one another, and wherein
 said base has a front surface that faces the pin when the pin is arranged between said clipping area of said first arm and said clipping area of said second arm, and a back surface that faces away from said front surface of said base;
 said at least one electrically conductive pin being clamped to said at least one clip by way of said clipping areas of said at least one clip,
 said clip including at least one wiring band integrally formed with said clip and extending from said first end and/or said second end, wherein said at least one wiring band has an electrically conductive connection to said connection socket in said header portion.

2. The medical device according to claim 1, wherein said clipping area of said first arm and said clipping area of said second arm are configured to be pretensioned against the pin to make the said connection when the pin is arranged between said clipping area of said first arm and said clipping area of said second arm.

3. The medical device according to claim 1, wherein:
 each of said centering area of said first arm and said centering area of said second arm has an inner surface, said inner surface of said centering area of said first arm facing towards said inner surface of said centering area of said second arm; and
 said first arm and said second arm are configured such that pressing the pin against said facing inner surfaces of said centering areas of said first and second arms presses said first and second arms apart, to enable the pin to be arranged between said clipping area of said first arm and said clipping area of said second arm.

4. The medical device according to claim 1, wherein said first arm and said second arm are integrally formed in one piece with said base.

5. The medical device according to claim 1, further comprising a further base connected via a connection area with said base.

6. The medical device according to claim 5, further comprising a third arm and a fourth arm opposite said third arm, each of said third and fourth arms having a clipping area, said clipping area of said third arm and said clipping area of said fourth arm running toward one another and being configured to lie against the pin to make the mechanical and electrically conductive connection when the pin is arranged between said clipping area of said third arm and said clipping area of said fourth arm, and a centering area departing from said clipping area of said third arm and a centering area departing from said clipping area of said fourth arm, said centering areas of said third arm and of said fourth arm diverging from one another.

7. The medical device according to claim 6, wherein said third and the fourth arms project out from said further base.

8. The medical device according to claim 6, wherein said base forms a welding area enabling the clip to be welded with the pin when the pin is arranged between said clipping area of said first arm and said clipping area of said second arm and/or said further base forms a further welding area enabling the clip to be welded with the pin when the pin is arranged between said clipping area of said third arm and said clipping area of said fourth arm.

9. The medical device according to claim 5, wherein said connection area has a front surface that faces the pin when the pin is arranged between said clipping areas of said arms, said front surface of said connection area being convexly curved to make contact with the pin.

10. The medical device according to claim 1, wherein said base forms a welding area enabling the clip to be welded with the pin when the pin is arranged between said clipping area of said first arm and said clipping area of said second arm.

\* \* \* \* \*